United States Patent
Puzankov et al.

(10) Patent No.: US 10,512,250 B2
(45) Date of Patent: Dec. 24, 2019

(54) OXALIC ACID VAPORIZER WITH INTEGRAL BODY TUBE, DETACHABLE PROXIMAL END AIR NOZZLE, AND FLOATING HEATING ELEMENT

(71) Applicants: Edik A. Puzankov, Carmichael, CA (US); Andrey Puzankov, Carmichael, CA (US); Daniel Khashchuk, Carmichael, CA (US)

(72) Inventors: Edik A. Puzankov, Carmichael, CA (US); Andrey Puzankov, Carmichael, CA (US); Daniel Khashchuk, Carmichael, CA (US)

( * ) Notice: Subject to any disclaimer, the term of this patent is extended or adjusted under 35 U.S.C. 154(b) by 352 days.

(21) Appl. No.: 15/585,291

(22) Filed: May 3, 2017

(65) Prior Publication Data

US 2018/0317458 A1    Nov. 8, 2018

(51) Int. Cl.
*A01M 1/20* (2006.01)
*A01K 51/00* (2006.01)
*A01N 37/04* (2006.01)

(52) U.S. Cl.
CPC ........... *A01K 51/00* (2013.01); *A01M 1/2022* (2013.01); *A01M 1/2061* (2013.01);
(Continued)

(58) Field of Classification Search
CPC ............. A01M 1/2061; A01M 1/2022; A01M 1/2072; A01M 1/2077; A01K 51/00; A01K 55/00
(Continued)

(56) References Cited

U.S. PATENT DOCUMENTS

| | | | | |
|---|---|---|---|---|
| 621,613 A | * | 3/1899 | Miller | ............... A01M 13/003 43/125 |
| 1,678,403 A | * | 7/1928 | Martin | ............... C07C 45/33 204/157.6 |

(Continued)

FOREIGN PATENT DOCUMENTS

| | | | |
|---|---|---|---|
| CA | 2295898 A1 | * | 7/2001 |
| DE | 10054048 A1 | * | 5/2002 |

(Continued)

OTHER PUBLICATIONS

Varrocleaner, OxaVap—Your Source of Oxalic Acid Vaporizers; Available web site: https://oxavap.com/product/varrocleaner-oxalic-acid-vaporizer/; created 2014; downloaded on Sep. 19, 2019. (Year: 2014).*

(Continued)

*Primary Examiner* — Darren W Ark
(74) *Attorney, Agent, or Firm* — Craig A. Simmermon

(57) ABSTRACT

Oxalic acid vaporizer with integral body tube, detachable proximal end air nozzle, and floating heating element is a pest control vaporizer or pesticide vaporizer that is used to protect bees from certain pests, mites, and insects where the pesticide vaporizer expels a vapor that kills harmful pests, mites, and insects but does not harm or affect bees in the colony. Oxalic acid vaporizer with integral body tube, detachable proximal end air nozzle, and floating heating element includes an integral body tube that is without any holes, perforations, punctures, gaps, vents, or discontinuities. Oxalic acid vaporizer with integral body tube, detachable proximal end air nozzle, and floating heating element includes a detachable proximal end air nozzle. Oxalic acid vaporizer with integral body tube, detachable proximal end air nozzle, and floating heating element includes a floating heating element with a floating electrical connection.

4 Claims, 3 Drawing Sheets

(52) U.S. Cl.
CPC ........ *A01M 1/2072* (2013.01); *A01M 1/2077* (2013.01); *A01N 37/04* (2013.01)

(58) Field of Classification Search
USPC .............. 43/129, 128, 127, 125, 124, 132.1; 219/201, 236–238; 239/133; 392/386, 392/465, 468, 471, 473, 476, 478–480
See application file for complete search history.

(56) References Cited

U.S. PATENT DOCUMENTS

| | | | | |
|---|---|---|---|---|
| 2,467,393 | A * | 4/1949 | Leher | F22B 1/284 392/401 |
| 2,685,146 | A * | 8/1954 | Stevens | A01M 13/00 43/129 |
| 2,758,412 | A * | 8/1956 | Loibl, Jr. | A01M 13/00 43/125 |
| 2,882,640 | A * | 4/1959 | Kopecky | A01M 1/2077 43/129 |
| 3,034,726 | A * | 5/1962 | Peras | B05B 1/24 239/132 |
| 3,069,092 | A * | 12/1962 | Norvell, Jr. | A01M 1/2077 239/133 |
| 3,132,067 | A * | 5/1964 | Knopke | A01N 25/26 424/405 |
| 3,134,191 | A * | 5/1964 | Davis | A01M 13/00 43/129 |
| 3,214,860 | A * | 11/1965 | Johnson | B65D 83/72 43/129 |
| 3,229,409 | A * | 1/1966 | Johnson | B05B 9/002 43/129 |
| 3,255,967 | A * | 6/1966 | Kenney | B05B 1/24 239/133 |
| 3,290,112 | A * | 12/1966 | Gillenwater | A61L 9/122 43/129 |
| 3,392,479 | A * | 7/1968 | Simmons | B05B 7/2464 43/129 |
| 3,421,841 | A * | 1/1969 | Wittwer | A01M 1/2077 43/129 |
| 3,458,948 | A * | 8/1969 | Schlensker | A01M 13/00 43/129 |
| 3,465,469 | A * | 9/1969 | Winter | B05B 7/168 43/129 |
| 3,496,668 | A * | 2/1970 | Slater | B05B 7/1686 43/129 |
| 3,623,260 | A * | 11/1971 | Konle | A01M 13/00 43/129 |
| 3,656,254 | A * | 4/1972 | Schmedes | A01M 13/00 43/129 |
| 3,675,360 | A * | 7/1972 | Pierce | A01M 1/2077 43/129 |
| 3,782,026 | A * | 1/1974 | Bridges | A01M 13/00 43/124 |
| 3,793,763 | A * | 2/1974 | Griffin | A01M 1/06 43/129 |
| 3,986,670 | A * | 10/1976 | Syveson | A01M 13/00 239/133 |
| 4,998,479 | A * | 3/1991 | Perham | F41H 9/06 102/329 |
| 5,069,651 | A * | 12/1991 | Arndt | A01K 51/00 449/12 |
| 5,282,334 | A * | 2/1994 | Kimura | A01M 1/2072 261/DIG. 89 |
| 5,335,446 | A * | 8/1994 | Shigetoyo | A01M 1/2033 43/125 |
| 6,361,752 | B1 * | 3/2002 | Demarest | A01M 1/2072 165/104.26 |
| 6,620,025 | B2 * | 9/2003 | Scheuneman | A01K 51/00 449/1 |
| 7,578,722 | B1 * | 8/2009 | Baumgartner | A01K 51/00 43/129 |
| 7,766,722 | B2 * | 8/2010 | Arndt | A01K 55/00 43/130 |
| 8,296,993 | B2 * | 10/2012 | Modlin | A01M 29/12 239/102.2 |
| 8,353,126 | B2 * | 1/2013 | Stearns | A01K 55/00 43/127 |
| RE44,312 | E * | 6/2013 | Vieira | A01M 1/2077 219/486 |
| 9,485,969 | B2 * | 11/2016 | Pelzel | A01K 55/00 |
| 9,655,346 | B2 * | 5/2017 | Semenov | B05B 7/1686 |
| 9,992,978 | B2 * | 6/2018 | Maher | A01K 51/00 |
| 2005/0262756 | A1 * | 12/2005 | Younger | A01K 55/00 43/128 |
| 2009/0010625 | A1 * | 1/2009 | Fowler | F24H 1/142 392/397 |
| 2010/0089893 | A1 * | 4/2010 | Schlipf | B29C 45/1782 219/201 |
| 2011/0253798 | A1 * | 10/2011 | Tucker | A61L 9/037 239/13 |
| 2016/0120225 | A1 * | 5/2016 | Mishra | A24F 47/008 392/386 |
| 2018/0263222 | A1 * | 9/2018 | Oster | A01K 51/00 |
| 2019/0141980 | A1 * | 5/2019 | Martens | A01M 1/2061 43/129 |
| 2019/0269811 | A1 * | 9/2019 | Trzecieski | A61M 15/08 |

FOREIGN PATENT DOCUMENTS

| | | | | |
|---|---|---|---|---|
| DE | 20212031 U1 * | 3/2003 | | |
| DE | 202007002266 U1 * | 5/2007 | | |
| DE | 202007001721 U1 * | 7/2007 | | |
| DE | 202015006704 U1 * | 12/2015 | | |
| EP | 218162 A2 * | 4/1987 | | |
| EP | 0259506 A1 * | 3/1988 | ............ | A01K 51/00 |
| KR | 20080024170 A * | 3/2008 | | |
| KR | 20110088193 A * | 8/2011 | | |
| RU | 2033046 C1 * | 4/1995 | | |
| SU | 1683605 A1 * | 10/1992 | | |
| WO | WO-0195707 A1 * | 12/2001 | ............ | A01K 51/00 |
| WO | WO-2014189233 A1 * | 11/2014 | | |
| WO | WO-2018116331 A1 * | 6/2018 | ............ | A01K 51/00 |

OTHER PUBLICATIONS

Scientific Beekeeping.com, Oxalic Acid: Heat Vaporization and Other Methods: Part 2 of 2 Parts; Available web site: http://scientificbeekeeping.com/oxalic-acid-heat-vaporization-and-other-methods-part-2-of-2-parts/; created Jan. 2007; downloaded on Sep. 18, 2019. (Year: 2007).*

Heilyser Technology, Heilyser Oxalic Acid Vaporizer; Available web site: http://www.heilysertechnology.com/vaporizer.html; created 1991; downloaded on Sep. 18, 2019. (Year: 1991).*

* cited by examiner

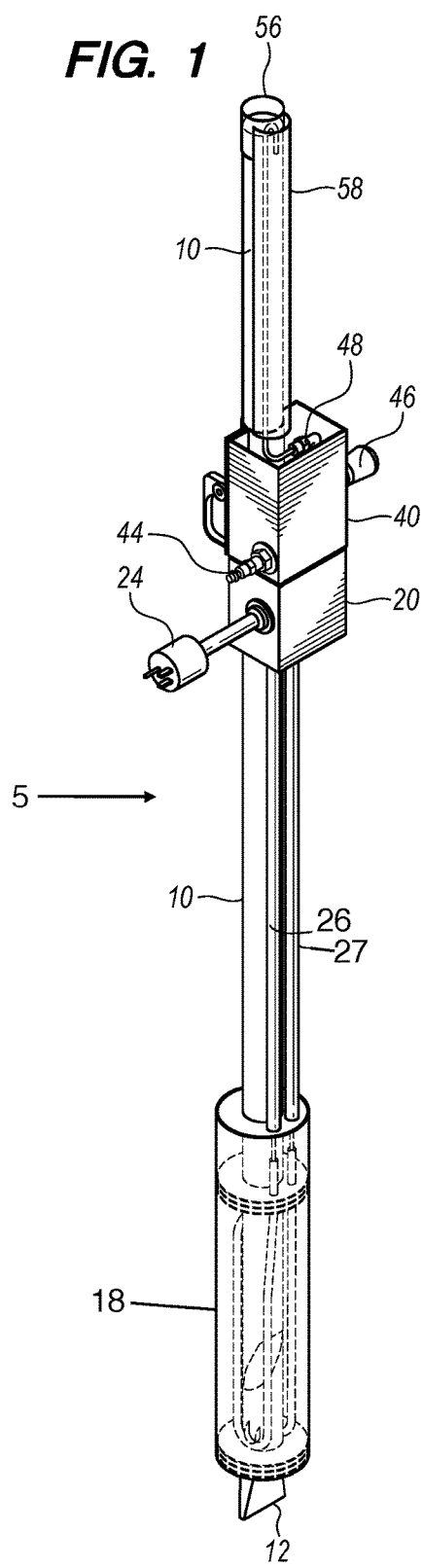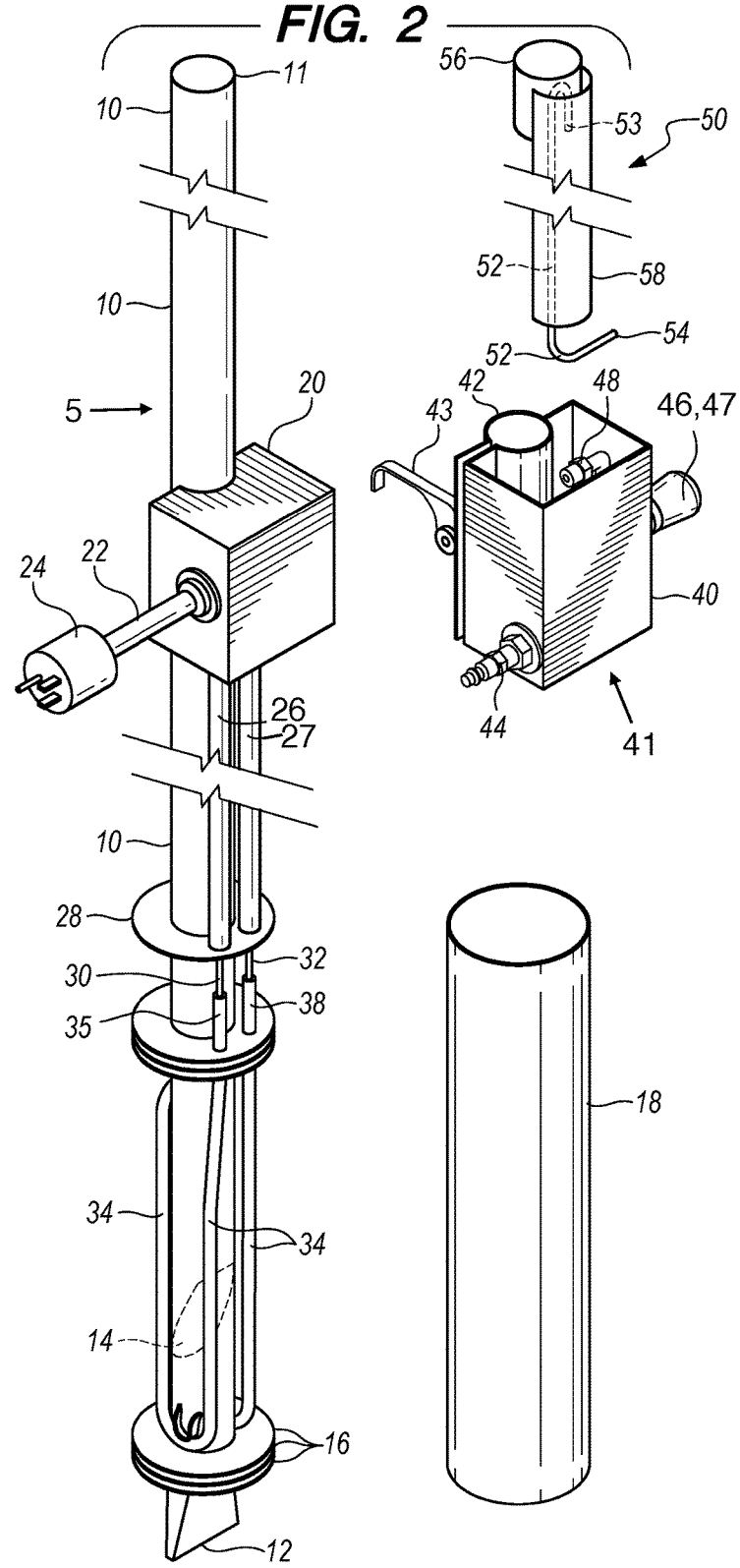

OXALIC ACID VAPORIZER WITH INTEGRAL BODY TUBE, DETACHABLE PROXIMAL END AIR NOZZLE, AND FLOATING HEATING ELEMENT

BACKGROUND OF THE INVENTION

1. Field of the Invention

This invention relates to a pest control vaporizer or pesticide vaporizer that is used to protect bees from certain pests, mites, and insects where the pesticide vaporizer expels a vapor that kills harmful pests, mites, and insects but does not harm or affect bees in the colony. Specifically, this invention is an oxalic acid vaporizer with an integral body tube, a detachable proximal end air nozzle, and a floating heating element that allows for easier use and maintenance of the bee vaporizer.

2. Description of Related Art

There are many bee vaporizers in the prior art; however, none have an integral body tube, a detachable proximal end air nozzle, or a floating heating element, which individually and collectively facilitate for much easier use and maintenance of the bee vaporizer.

BRIEF SUMMARY OF THE INVENTION

It is an aspect of oxalic acid vaporizer with integral body tube, detachable proximal end air nozzle, and floating heating element to include an airtight integral body tube that is without holes, punctures, gaps, vents, or discontinuities.

It is an aspect of oxalic acid vaporizer with integral body tube, detachable proximal end air nozzle, and floating heating element to include a detachable proximal end air nozzle that may be completely detached from the integral body tube and reattached to the integral body tube.

It is an aspect of oxalic acid vaporizer with integral body tube, detachable proximal end air nozzle, and floating heating element to include a detachable proximal end air nozzle that is removeably attachable to the proximal end of integral body tube.

It is an aspect of oxalic acid vaporizer with integral body tube, detachable proximal end air nozzle, and floating heating element to include a detachable pneumatic box that may be completely detached from the exterior of the integral body tube and reattached to the integral body tube.

It is an aspect of oxalic acid vaporizer with integral body tube, detachable proximal end air nozzle, and floating heating element to include a detachable pneumatic box that is removeably attachable to the exterior of integral body tube.

It is an aspect of detachable proximal end air nozzle to inject air into the proximal end of integral body tube and not within the mid-section of the integral body tube.

It is an aspect of oxalic acid vaporizer with integral body tube, detachable proximal end air nozzle, and floating heating element to include a floating heating element that is slideably attached to the exterior of integral body tube where this slideable attachment prevents any stress build-up on the attachment means resulting from thermal expansion and contraction of the heating element.

It is an aspect of floating heating element to have a sliding or floating attachment means that allows the heating element to slide longitudinally along the longitudinal axis of integral body tube.

It is an aspect of floating heating element to have windings that run longitudinally along the longitudinal axis of integral body tube and not laterally along the longitudinal axis of integral body tube.

It is an aspect of the means of slideable attachment of floating heating element to allow for longitudinal sliding or longitudinal expansion and contraction of the floating heating element without stressing the means of slideable attachment to integral body tube.

It is an aspect of slideable attachment of floating heating element to include at least two special floating heating element saddles that hold one end of floating heating element fixed onto integral body tube but allow for the other end of floating heating element to slide longitudinally back and forth.

BRIEF DESCRIPTION OF THE DRAWINGS

FIG. 1 is a perspective view of oxalic acid vaporizer with integral body tube, detachable proximal end air nozzle, and floating heating element.

FIG. 2 is an exploded view of oxalic acid vaporizer with integral body tube, detachable proximal end air nozzle, and floating heating element.

DEFINITION LIST

Figure 3:
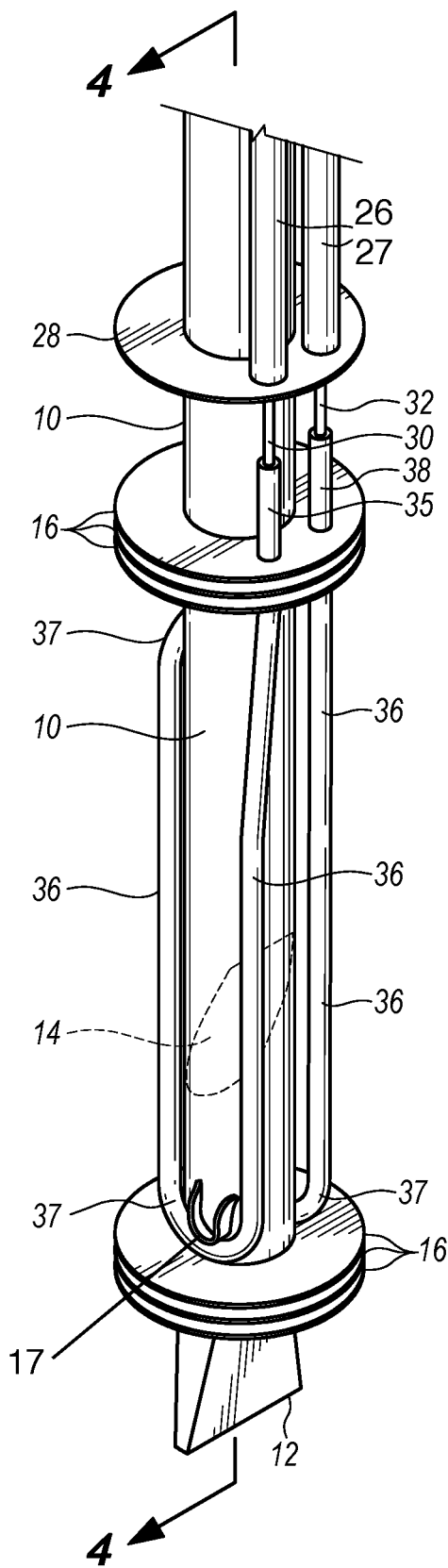
FIG. 3 is an enlarged view of the distal end of oxalic acid vaporizer with integral body tube, detachable proximal end air nozzle, and floating heating element that defines cross-sectional plane 4-4.
Figure 4:
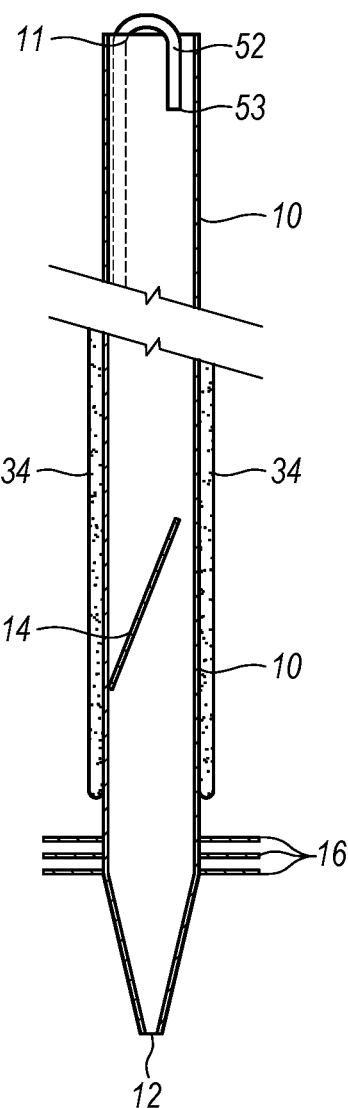
FIG. 4 is a cross-sectional view taken from lines 4-4 in FIG. 3.
Figure 5:
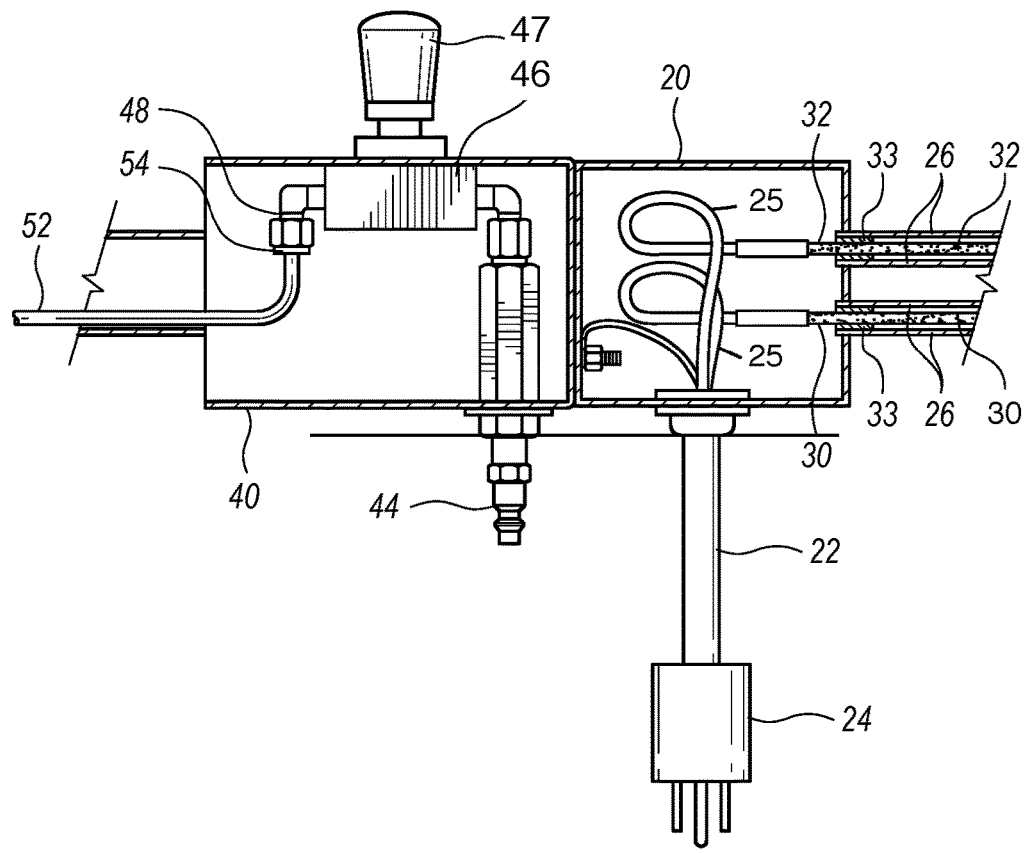
FIG. 5 is an enlarged cross-sectional view of the middle section of oxalic acid vaporizer with integral body tube, detachable proximal end air nozzle, and floating heating element depicting the interior of electrical box and the interior of detachable pneumatic box.
Figure 6:
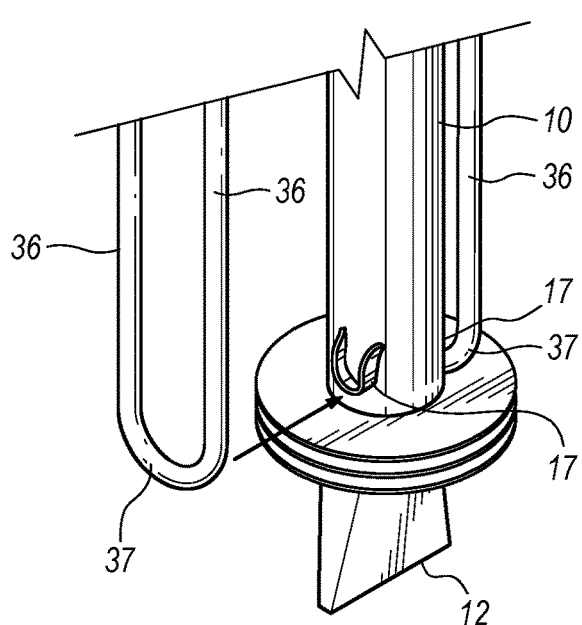
FIG. 6 is an enlarged and partially exploded view of FIG. 3, depicting how floating heating element is slideably attached to a floating heating element saddle and to the exterior of integral body tube.
Figure 7:
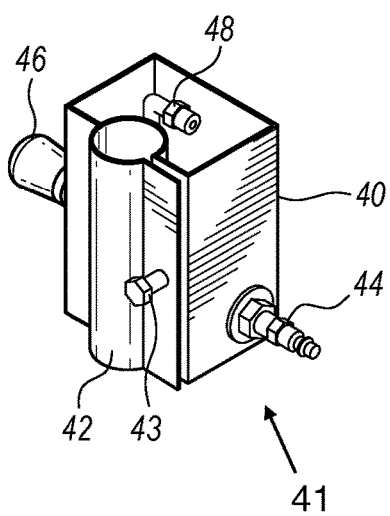
FIG. 7 is a perspective view of detachable pneumatic box assembly after it has been detached from the exterior of integral body tube.

| Term | Definition |
| --- | --- |
| 5 | Oxalic acid vaporizer with integral body tube, detachable proximal end air nozzle, and floating heating element |
| 10 | Integral Body Tube |
| 11 | Proximal End of Integral Body Tube |
| 12 | Distal End of Integral Body Tube |
| 14 | Internal Powder Baffle |
| 16 | External Heat Baffle |
| 17 | Floating Heating Element Saddle |
| 18 | Outer Heat Shield |
| 20 | Electrical Box |
| 22 | Power Cord |
| 24 | Power Connector |
| 25 | Internal Electrical Wiring |
| 26 | First Floating Conductor Rod Electrical Shield |
| 27 | Second Floating Conductor Rod Electrical Shield |
| 28 | Floating Heating Element Electrical Shield |
| 30 | First Floating Conductor Rod |
| 32 | Second Floating Conductor Rod |
| 33 | Floating Conductor Rod Slide Bushing |
| 34 | Floating Heating Element |
| 35 | First End of Floating Heating Element |
| 36 | Longitudinal Segment of Floating Heating Element |
| 37 | Ninety-Degree Segment of Floating Heating Element |
| 38 | Second End of Floating Heating Element |
| 40 | Detachable Pneumatic Box |
| 41 | Detachable Pneumatic Box Assembly |
| 42 | Pneumatic Box Clamp |

| Term | Definition |
| --- | --- |
| 43 | Clamp Handle or Fastener |
| 44 | Air Hose Connector |
| 46 | Pneumatic Valve |
| 47 | Valve Handle |
| 48 | Nozzle Tube Fitting |
| 50 | Detachable Proximal End Air Nozzle Assembly |
| 52 | Nozzle Tube |
| 53 | Proximal End of Nozzle Tube |
| 54 | Distal End of Nozzle Tube |
| 56 | Locating Collar |
| 58 | Nozzle Tube Shield |

DETAILED DESCRIPTION OF THE INVENTION

Oxalic acid vaporizer with integral body tube, detachable proximal end air nozzle, and floating heating element 5 comprises an integral body tube 10. Integral body tube 10 is a rigid hollow cylindrical member with a diameter of about 1 to 10 inches and a length of about 2 to 10 feet. The side or sides of cylindrical member is airtight and without any holes, perforations, punctures, gaps, vents, or discontinuities. The thickness of the rigid hollow cylindrical member is about $\frac{1}{16}$ to $\frac{3}{8}$ inches. Integral body tube 10 has an interior surface, an exterior surface, and a longitudinal axis running along the length of the rigid hollow cylindrical member. Integral body tube 10 is made of a material that is resistant to high temperatures and can withstand high temperatures without degrading such as metal, steel, ceramic, fiberglass, composite, porcelain, or similar. Integral body tube 10 has a proximal end 11 and a distal end 12. The proximal end 11 is most near the operator of the oxalic acid vaporizer with integral body tube, detachable proximal end air nozzle, and floating heating element 5. The distal end 12 is most distant to the operator of the oxalic acid vaporizer with integral body tube, detachable proximal end air nozzle, and floating heating element 5. The proximal end 11 of integral body tube 10 is open and is a circular opening on the end of the rigid hollow cylindrical member. The distal end 12 of integral body tube 10 is pinched or narrowed to form an open slotted end on the rigid hollow cylindrical member. Open slot may be formed out of integral body tube 10 or may be a separate fitting that is attached to integral body tube 10. During operation of the oxalic acid vaporizer with integral body tube, detachable proximal end air nozzle, and floating heating element 5, oxalic acid vapor is forced or propelled from or out of open slotted end at distal end 12 of the rigid hollow cylindrical member.

Importantly, integral body tube 10 is a solid member without any holes, perforations, punctures, gaps, vents, or discontinuities in the rigid cylindrical member. Existing body tubes on existing oxalic acid vaporizers have a hole, perforation, gap, or vent in the mid-section of the body tube in order to provide access for the air nozzle. Existing oxalic acid vaporizers locate their air nozzle at the mid-section of the body tube and not at an end of the body tube. This design is not preferred because a mid-section mounted air nozzle located in the middle of the body tube has a tendency to cause or allow for the collection or build-up of oxalic acid vapor, oxalic acid powder, and/or burnt oxalic acid powder on the air nozzle and on the interior of the body tube in the vicinity of the air nozzle. Oxalic acid vapor, oxalic acid powder, and burnt oxalic acid powder build-up can cause blockage or clogging of the body tube that can cut off airflow through the body tube and out of the distal end of the body tube to render the oxalic acid vaporizer inoperable and useless. Blockage or clogging of the body tube necessitates disassembly of oxalic acid vaporizer in order to clean out the blockage or clog and to render the oxalic acid vaporizer operable and useful again. As detailed below, this invention incorporates a superior design that uses a detachable proximal end air nozzle assembly 50 located at the proximal end 11 of integral body tube 10, which allows for quick and easy detachment of detachable proximal end air nozzle assembly 50 from integral body tube 10 to provide for much easier cleanups and de-clogging of the oxalic acid vaporizer 5 where blockages and clogging occur on a removable nozzle and at the end of the body tube and not in the middle of the body tube.

Oxalic acid vaporizer with integral body tube, detachable proximal end air nozzle, and floating heating element 5 further comprises an internal powder baffle 14 attached to the interior surface of integral body tube 10. Internal powder baffle 14 is a rigid oblong planar member with a left sides, a right sides, a lower end, and an upper end, and a longitudinal axis running through the lower and upper ends. Internal powder baffle 14 is located within integral body tube 10 so that its longitudinal axis is askew from that of integral body tube 10 by about 15-75 degrees. The left sides, the right sides, and lower end of internal powder baffle 14 are each rigidly attached or connected to the interior surface of integral body tube 10 while the upper end of internal powder baffle 14 is not attached or connected to the interior surface of integral body tube 10. Rigid attachment must be impermeable to oxalic acid powder. This design yields a step, ledge, shelf, or chamber inside integral body tube 10 as depicted. Internal powder baffle 14 functions to provide a step, ledge, shelf, or chamber on which oxalic acid powder (not depicted) is loaded and stored for use during operation of the oxalic acid vaporizer with integral body tube, detachable proximal end air nozzle, and floating heating element 5. During operation of the oxalic acid vaporizer with integral body tube, detachable proximal end air nozzle, and floating heating element 5, oxalic acid powder stored and resting on internal powder baffle 14 is heated and vaporized where compressed air is then blown across the vapor to be forced downward and ejected out of the distal end 12 of integral body tube 10. Oxalic acid powder sublimes or changes from a solid state to a gaseous state at a temperature of about 370-400 degrees Fahrenheit. Thus, the internal powder baffle area must maintain a temperature of at least 370-400 degrees Fahrenheit.

Oxalic acid vaporizer with integral body tube, detachable proximal end air nozzle, and floating heating element 5 further comprises at least two floating heating element saddles 17. Each floating heating element saddle 17 is a rigid arch-shaped, bow-shaped, or U-shaped member with a concave side and a convex side. Each floating heating element saddle 17 is rigidly attached to the exterior surface of integral body tube 10, near the distal end 12 integral body tube 10, and oriented so that the concave side of each floating heating element saddle 17 is aligned with the longitudinal axis of the integral body tube 10 and faces the proximal end 11 of integral body tube 10, and the convex side of each floating heating element saddle 17 is aligned with the longitudinal axis of the integral body tube 10 faces the distal end 12 of integral body tube 10, as depicted. At least two floating heating element saddles 17 comprise: a first and a second floating heating element saddle 17. First and second floating heating element saddles 17 are located opposite sides of integral body tube 10. At least two floating heating element saddles 17 function to help locate and attach floating heating element 34 to integral body tube 10 in such a way as to allow for longitudinal movement or longitudinal sliding to occur between floating heating element 34 and integral body tube 10 along the longitudinal axis of integral body tube 10 as floating heating element 34 expands as a result of thermal expansion when floating heating element 34 is turned on and heated up. Floating heating element 34 must be turned on and heated up in order to operate oxalic acid vaporizer with integral body tube, detachable proximal end air nozzle, and floating heating element 5.

Oxalic acid vaporizer with integral body tube, detachable proximal end air nozzle, and floating heating element 5 further comprises a floating heating element 34. Floating heating element 34 is a heating element that converts electricity into heat through the process of resistive or Joule heating where electric current passing through the element encounters resistance, resulting in heating of the element. Any know type of heating element may be used. In best mode, floating heating element is a custom-shaped tubular heater. Floating heating element 34 is continuous heating element that is wound and formed in a special shape to form a cylindrical shape with open ends. Cylindrical shape has an inner diameter sized to make a slip fit or press fit with the exterior surface of integral body tube 10. Floating heating element 34 has longitudinal windings that longitudinally wind or wrap around the exterior surface of integral body tube 10 as depicted. Heating elements with longitudinal windings have heating segments that run longitudinally along the longitudinal axis of the vaporizer body tube, while lateral windings have heating segments that run essentially perpendicular to the longitudinal axis of the vaporizer body tube. Longitudinal windings are preferred over lateral windings because thermal expansion causes heating elements with lateral windings to expand radially outward from and away from contact with the vaporizer body tube, which is detrimental to heat transfer, heat conduction, and the operation of the vaporizer. On the other hand, thermal expansion does not cause heating elements with longitudinal windings to loose contact with the body tube as the expansion occurs longitudinally, which allows for the heating element to remain in contact with the vaporizer body tube.

Floating heating element 34 comprises: a first end 35, at least four longitudinal segments 36, at least three ninety-degree segments 37, and a second end 38. First end 35 and second end 38 are each straight sections or segments that run longitudinally and parallel with the longitudinal axis of integral body tube 10. Each longitudinal segment 36 is a section or segment of floating heating element 34 running parallel to the longitudinal axis of integral body tube 10. Each longitudinal segment 36 has a proximal end and a distal end. Each ninety-degree segment 37 is a U-shaped section or segment of floating heating element 34 that is a 90-degree bend in the heating element with a concave side and a convex side. The concave side of each U-shaped section is sized to make a slip fit or press fit with the convex side of each floating heating element saddle 17. Each ninety-degree segment 37 has an A end and a B end where the A end is connected to a longitudinal segment 36 and the B end is connected to different longitudinal segment 36. First end 35, at least four longitudinal segments 36, at least three ninety-degree segments 37, and a second end 38 are contiguous and are all a portion of one continuous heating element where each segment is in electrical continuity with all other segments. There is a first, second, third, and fourth longitudinal segment 36. There is a first, second, and third ninety-degree segment 37. The proximal end of first longitudinal segment 36 is connected to the first end 35 of floating heating element 34. The distal end of first longitudinal segment 36 is connected to the A end of a first ninety-degree segment 37. The distal end of the second longitudinal segment 36 is connected to the B end of first ninety-degree segment 37. The proximal end of second longitudinal segment 36 is connected to the A end of second ninety-degree segment 37. The proximal end of third longitudinal segment 36 is connected to the B end of second ninety-degree segment 37. The distal end of third longitudinal segment 36 is connected to the A end of third ninety-degree segment 37. The distal end of fourth longitudinal segment 36 is connected to the B end of third ninety-degree segment 37. The proximal end of fourth longitudinal segment 36 is connected to the second end 38 of floating heating element 34. The first and third ninety-degree segments 37 are oriented with their concave side aligned with the longitudinal axis of integral body tube 10 and directly facing the proximal end of oxalic acid vaporizer with integral body tube, detachable proximal end air nozzle, and floating heating element 5. The second ninety-degree segment 37 is oriented with its concave side aligned with the longitudinal axis of integral body tube 10 and directly facing the distal end of oxalic acid vaporizer with integral body tube, detachable proximal end air nozzle, and floating heating element 5.

Floating heating element 34 is located onto the exterior surface of integral body tube 10 and slideably attached to the exterior surface of integral body tube 10 by first and second floating heating element saddles 17. First and second floating heating element saddles are identical. Floating heating element 34 is located onto the first and second floating heating element saddles 17 so that the convex side of the first floating heating element saddle 17 is nested within and aligned with the concave side of the first ninety-degree segment 37 of floating heating element 34 and the convex side of the second floating heating element saddle 17 is nested within and aligned with the concave side of the third ninety-degree segment 37 of floating heating element 34. The concave side of the first ninety-degree segment 37 is press fit or slip fit onto the convex side of first floating heating element saddle 17. The concave side of the third ninety-degree segment 37 is press fit or slip fit onto the convex side of second floating heating element saddle 17. The second ninety-degree segment 37 of floating heating element 34 is not attached to a floating heating element saddle 17 and may slide along the exterior surface thereof as a result of thermal expansion and contraction. The first end 35 and second end 38 of floating heating element 34 are not attached to the integral body tube 10 and may slide along the exterior surface thereof as a result of thermal expansion.

Alternately, a third floating heating element saddle 17 may be used to locate floating heating element 34 onto the exterior surface of integral body tube 10 and to slideably attach floating heating element 34 to the exterior surface of integral body tube 10. The third floating heating element saddle 17 is rigidly attached to the exterior surface of integral body tube 10 and oriented so that the convex side of the third floating heating element saddle 17 is aligned with the longitudinal axis of the integral body tube 10 and faces the proximal end 11 of integral body tube 10. The third floating heating element saddle 17 is located so that the concave side of the second ninety-degree segment 37 press fits or slip fits onto the convex side of third floating heating element saddle 17 when the heating element is cold. In this alternate design, thermal expansion primarily yields a meandering of the heating element between floating heating element saddles 17, where the floating heating element saddles 17 more or less hold all ninety-degree segments 37 still, forcing the longitudinal segments 36 grow in length, yielding bowing or flexing of the longitudinal segments 36 when hot, which is dubbed meandering of the heating element between floating heating element saddles 17.

Oxalic acid vaporizer with integral body tube, detachable proximal end air nozzle, and floating heating element 5 further comprises a plurality of external heat baffles 16. Each external heat baffle 16 is a rigid planar annular shaped member or ring shaped member with an inner diameter and an out diameter. The inner diameter is sized to make a slip fit or press fit with the exterior surface of the integral body tube 10. The outer diameter is sized to make a slip fit or press fit with the interior surface of outer heat shield 18. Each external heat baffle 16 has a thickness of about $1/16$ to $3/8$ inches. Each external heat baffle 16 is made of a material that is resistant to high temperatures and can withstand high temperatures without degrading such as metal, steel, ceramic, fiberglass, composite, porcelain, or similar. Each external heat baffle 16 is positioned with its plane perpendicular to the longitudinal axis of integral body tube 10.

Plurality of external heat baffles 16 comprises a distal plurality of external heat baffles 16 located adjacent to the convex sides of the first and third ninety-degree segments 37 at the distal end of integral body tube 10, as depicted. The proximal side of the most proximal external heat baffle 16 of this plurality is in contact with the convex sides of the first and third ninety-degree segments 37. Location is such that the first ninety-degree segment 37 is sandwiched between the convex side of first floating heating element saddle 17 and the proximal side of the most proximal external heat baffle 16 of this plurality of external heat baffles 16, and the third ninety-degree segment 37 is sandwiched between the convex side of second floating heating element saddle 17 and the proximal side of the most proximal external heat baffle 16 of this plurality of external heat baffles 16.

Plurality of external heat baffles 16 comprises a proximal plurality of external heat baffles 16 located above the convex side of the second ninety-degree segment 37 with a space in between as depicted. This space is provided to allow clearance room for thermal expansion and contraction or longitudinal sliding of floating heating element 34. This design precludes thermal expansion and contraction or longitudinal sliding of floating heating element 34 at the distal end of floating heating element 34 and forces all thermal expansion and contraction and longitudinal sliding of floating heating element 34 to occur at the proximal end of floating heating element 34. The optional third floating heating element saddle 17 is located on the distal side of the most distal external heat baffle 16 in the proximal plurality of external heat baffles 16.

Oxalic acid vaporizer with integral body tube, detachable proximal end air nozzle, and floating heating element 5 further comprises a floating heating element electrical shield 28. Floating heating element electrical shield 28 is a rigid annular shaped member or ring shaped member with an inner diameter and an out diameter. The inner diameter is sized to make a slip fit or press fit with the exterior surface of the integral body tube 10. The outer diameter is sized to make a slip fit or press fit with the interior surface of outer heat shield 18. Floating heating element electrical shield 28 has a thickness of about $1/16$ to $3/8$ inches. Floating heating element electrical shield 28 is made of a material that is resistant to high temperatures and can withstand high temperatures without degrading such as metal, steel, ceramic, fiberglass, composite, porcelain, or similar. Floating heating element electrical shield 28 is positioned adjacent to the first and second ends 35,38 of floating heating element 34 with its plane perpendicular to the longitudinal axis of integral body tube 10. Floating heating element electrical shield 28 is positioned on the proximal side of first and second ends 35,38 of floating heating element 34 with its plane perpendicular to the longitudinal axis of integral body tube 10. Floating heating element electrical shield 28 has an upper surface located on its proximal end and a lower surface located on its distal end. Floating heating element electrical shield 28 functions to protect and shield the electrical connect between first floating conductor rod 30 and first end 35 of floating heating element 34 and the electrical connect between second floating conductor rod 32 and second end 38 of floating heating element 34.

Oxalic acid vaporizer with integral body tube, detachable proximal end air nozzle, and floating heating element 5 further comprises an outer heat shield 18. Outer heat shield 18 is a rigid hollow cylindrical member with open ends and a thickness of about $1/16$ to $3/8$ inches. Outer heat shield 18 has an interior surface, an exterior surface, and a longitudinal axis running along the length of the rigid hollow cylindrical member. The inner diameter of outer heat shield 18 is sized to make a slip fit or press fit with the outer diameter of each external heat baffle 16. The length of outer heat shield 18 is sized to span the distance between the floating heating element electrical shield 28 and the distal most external heat baffle 16. Outer heat shield 18 is made of a material that is resistant to high temperatures and can withstand high temperatures without degrading such as metal, steel, ceramic, fiberglass, composite, porcelain, or similar.

Outer heat shield 18 is sized, positioned, and located so that it covers floating heating element 34 and all external heat baffles 16 to form a heating element chamber that is defined by the exterior surface of integral body tube 10, the interior surface of outer heat shield 18, the plurality external heat baffles 16 located on the proximal end of floating heating element 34, and the plurality of external heat baffles 16 located on the distal end of floating heating element 34. Heating element chamber functions to help retain heat around floating heating element 34 during operation of the Oxalic acid vaporizer with integral body tube, detachable proximal end air nozzle, and floating heating element 5. Heat must be retained around the floating heating element 34 in order to keep the oxalic acid powder loaded onto internal powder baffle 14 in a continuous state of sublimation and also to prevent excessive heat from travelling upwards to the proximal end 11 of integral body tube 10 where the operator must handle the Oxalic acid vaporizer with integral body tube, detachable proximal end air nozzle, and floating heating element 5 in order to operate it. The proximal end 11 of integral body tube 10 must not become too hot to handle and operate. The above-described design with floating heating element 34 and at least two floating heating element saddles 17 greatly extends the lifetime of the vaporizer and is a far superior design to previous vaporizers that do not include a floating heating element 34 or at least two floating heating element saddles 17.

Oxalic acid vaporizer with integral body tube, detachable proximal end air nozzle, and floating heating element 5 further comprises: an electrical box 20, a power cord 22, a power connector 24, and internal electrical wiring 25. Electrical box 20 is a rigid hollow enclosure to house and protect internal electrical wiring 25. Electrical box 20 can be any type of protective enclosure to house and protect electrical wires. An electrical box 20 is typically required by safety codes. Electrical box 20 could be any know type of electrical box. Electrical box 20 has and interior and an exterior.

Electrical box 20 is rigidly attached to the exterior surface of integral body tube 10 in between the mid-section of integral body tube 10 and the proximal end of integral body tube 10. Electrical box 20 has an upper surface located on its exterior proximal end and a lower surface located on its exterior distal end. There is no electrical wiring or electrical components inside the interior of integral body tube 10. Power cord 22 is a standard electrical power cord with a first end and a second end. In best mode, power cord 22 is a standard power cord or extension cord for standard 115 Volt alternating current used in U.S. households. Power connector 24 is an electrical connector that is capable of connecting to a power source (not depicted). Power connector 24 is an electrical connector that plugs into or mates with an electrical connector on a power source. In best mode, power source is a 115 Volt alternating current portable generator that is located in close proximity to the beehives and power connector 24 is a standard male 115 Volt plug that plugs into or connects to the portable generator. Electrical power is required for the operation of oxalic acid vaporizer with integral body tube, detachable proximal end air nozzle, and floating heating element 5. Power connect 24 is connected to the first end of power cord 22 and is in electrical continuity with the first end of power cord 22. Internal electrical wiring 25 is connected to the second end of power cord 22 and is in electrical continuity with the second end of power cord 22. Internal electrical wiring 25 functions to provide electrical connections to first and second floating conductor rods 30,32. Internal electrical wiring 25 functions to provide to provide electrical continuity between power cord 22 and first floating conductor rod 30 and between power cord 22 and second floating conductor rod 32.

Oxalic acid vaporizer with integral body tube, detachable proximal end air nozzle, and floating heating element 5 further comprises: a first floating conductor rod electrical shield 26 and a second floating conductor rod electrical shield 27. First and second floating conductor rod electrical shields 26,27 are each a rigid hollow cylindrical member with open ends and a thickness of about 1/16 to 3/8 inches. First and second floating conductor rod electrical shields 26,27 each have an inner diameter, an outer diameter, an interior surface, an exterior surface, and a longitudinal axis running along the length of the rigid hollow cylindrical member. The inner diameter of first and second floating conductor rod electrical shields 26,27 is sized to make a slip fit or press fit with the outer diameter of floating conductor rod slide bushings 33. The length of first and second floating conductor rod electrical shields 26,27 is sized to span the distance between the lower surface of electrical box 20 and the upper surface of floating heating element electrical shield 28. First and second floating conductor rod electrical shields 26,27 are made of a material that is resistant to high temperatures and can withstand high temperatures without degrading such as metal, steel, ceramic, fiberglass, composite, porcelain, or similar.

First and second floating conductor rod electrical shields 26,27 are positioned and located so that their longitudinal axes are parallel with the longitudinal axis of integral body tube 10. First and second floating conductor rod electrical shields 26,27 are each positioned and located adjacent to the exterior surface of integral body tube 10 with an air space of about 0.25-5 inches in between the exterior surface of integral body tube 10 and the exterior surfaces of first and second floating conductor rod electrical shields 26,27.

First and second floating conductor rod electrical shields 26,27 are each a rigidly attached to the lower surface of electrical box 20 and to the upper surface of floating heating element electrical shield 28. Rigid attachment could be accomplished by welding, soldering, fastening, riveting, gluing, fusing, epoxy, or similar. There is a circular hole through floating heating element electrical shield 28 that is coincident with the longitudinal axis of first floating conductor rod electrical shield 26 where the diameter of the circular hole is the same as the inner diameter of first floating conductor rod electrical shield 26. There is a circular hole through the lower surface of electrical box 20 that is coincident with the longitudinal axis of first floating conductor rod electrical shield 26 where the diameter of the circular hole is the same as the inner diameter of first floating conductor rod electrical shield 26. With this design, the proximal end of first floating conductor rod 30 may be longitudinally threading through the circular hole in the floating heating element electrical shield 28, through the inside of first floating conductor rod electrical shield 26, and through the circular hole in the lower surface of electrical box 20. There is a circular hole through floating heating element electrical shield 28 that is coincident with the longitudinal axis of second floating conductor rod electrical shield 27 where the diameter of the circular hole is the same as the inner diameter of second floating conductor rod electrical shield 27. There is a circular hole through the lower surface of electrical box 20 that is coincident with the longitudinal axis of second floating conductor rod electrical shield 27 where the diameter of the circular hole is the same as the inner diameter of second floating conductor rod electrical shield 27. With this design, the proximal end of second floating conductor rod 32 is longitudinally threading through the circular hole in the floating heating element electrical shield 28, through the inside of second floating conductor rod electrical shield 27, and through the circular hole in the lower surface of electrical box 20.

Oxalic acid vaporizer with integral body tube, detachable proximal end air nozzle, and floating heating element 5 further comprises: a first floating conductor rod 30 and a second floating conductor rod 32. First and second floating conductor rods 30,32 are each a rigid solid cylindrical member with a diameter, a proximal end, a distal end, and a longitudinal axis running along the length of the rigid solid cylindrical member. First and second floating conductor rods 30,32 each have a length of about 0.5-5 feet. First and second floating conductor rods 30,32 each have a diameter of about 0.10 to 1 inches. First and second floating conductor rods 30,32 are each made of an electrically conductive material such as metal, graphite, or carbon. First and second floating conductor rods 30,32 are each heavy-duty rods that will not bend, bow, or laterally flex from thermal expansion and contraction. First and second floating conductor rods 30,32 are each heavy-duty rods that will not bend, bow, or laterally flex as a result of thermal stress. First and second floating conductor rods 30,32 are each located on the exterior side of integral body tube 10 with their longitudinal axes running parallel with the longitudinal axis of integral body tube 10 as depicted. First and second floating conductor rods 30,32 each function to pass electrical current and voltage from the electrical box 20 to floating heating element 34. Floating heating element 34 must be connected to an electrical power circuit or have an electrical power supply of electrical current and voltage in order to heat up and function. First and second floating conductor rods 30,32 supply this electrical current and voltage by transferring such from the electrical box 20 to the first and second ends 35,38 of floating heating element 34.

Oxalic acid vaporizer with integral body tube, detachable proximal end air nozzle, and floating heating element 5 further comprises at least four floating conductor rod slide bushings 33. Each floating conductor rod slide bushing 33 is a bushing or a washer. Each floating conductor rod slide bushing 33 is an annular shaped member or ring shaped member with an outside diameter, an inside diameter, and a thickness of about 0.10 to 1 inches. The outside diameter is sized to make a press-fit with the inside diameter of first and second floating conductor rod electrical shields 26,27. The inside diameter is sized to make a slip-fit with the outside diameter of first and second floating conductor rods 30,32. Each floating conductor rod slide bushing 33 is made of a non-conductive material or insulator material such as glass, ceramic, fiberglass, wood, paper, plastic, polymer, composite, fabric, or similar.

Two of at least four floating conductor rod slide bushings 33 are used to slideably attach first floating conductor rod 30 to the interior surface of first floating conductor rod electrical shield 26. First floating conductor rod 30 is slideably attached to the interior surface of first floating conductor rod electrical shield 26 with at least two floating conductor rod slide bushings 33. One floating conductor rod slide bushing 33 is positioned on the distal half of first floating conductor rod electrical shield 26. The other floating conductor rod slide bushing 33 is positioned on the proximal half of first floating conductor rod electrical shield 26. In best mode, there are four floating conductor rod slide bushings 33 evenly spaced along the entire length of first floating conductor rod electrical shield 26.

Two of at least four floating conductor rod slide bushings 33 are used to slideably attach second floating conductor rod 32 to the interior surface of second floating conductor rod electrical shield 27. Second floating conductor rod 32 is slideably attached to the interior surface of second floating conductor rod electrical shield 27 with at least two floating conductor rod slide bushings 33. One floating conductor rod slide bushing 33 is positioned on the distal half of second floating conductor rod electrical shield 27. The other floating conductor rod slide bushing 33 is positioned on the proximal half end of second floating conductor rod electrical shield 27. In best mode, there are four floating conductor rod slide bushings 33 evenly spaced along the entire length of second floating conductor rod electrical shield 27.

In order to slideably attach first floating conductor rod 30 to the interior surface of first floating conductor rod electrical shield 26, the proximal end of first floating conductor rod 30 is threaded through the floating conductor rod slide bushing 33 at the distal half of first floating conductor rod electrical shield 26, then through the floating conductor rod slide bushing 33 at the proximal half of first floating conductor rod electrical shield 26, and then into the interior of electrical box 20, as depicted. The proximal end of first floating conductor rod 30 is rigidly attached to internal electrical wiring 25. Rigid attachment is such that there is electrical conductivity and continuity between first floating conductor rod 30 and internal electrical wiring 25. Rigid attachment could be accomplished by welding, soldering, fastening, riveting, gluing, fusing, epoxy, or similar. Internal electrical wiring 25 includes plenty of slack to allow for thermal expansion and contraction of first floating conductor rod 30 without losing electrical continuity or breaking the electrical connection.

In order to slideably attach second floating conductor rod 32 to the interior surface of second floating conductor rod electrical shield 27, the proximal end of second floating conductor rod 32 is threaded through the floating conductor rod slide bushing 33 at the distal half of second floating conductor rod electrical shield 27, then through the floating conductor rod slide bushing 33 at the proximal half of second floating conductor rod electrical shield 27, and then into the interior of electrical box 20, as depicted. The proximal end of second floating conductor rod 32 is rigidly attached to internal electrical wiring 25. Rigid attachment is such that there is electrical conductivity and continuity between second floating conductor rod 32 and internal electrical wiring 25. Rigid attachment could be accomplished by welding, soldering, fastening, riveting, gluing, fusing, epoxy, or similar. Internal electrical wiring 25 includes plenty of slack to allow for thermal expansion and contraction of second floating conductor rod 32 without losing electrical continuity or breaking the electrical connection.

The distal end of first floating conductor rod 30 is rigidly attached to the first end 35 of floating heating element 34. Rigid attachment is end-to-end such that the longitudinal axis of first floating conductor rod 30 is coincident with the longitudinal axis of first end 35 of floating heating element 34. Rigid attachment is such that there is electrical conductivity and continuity between first floating conductor rod 30 and first end 35 of floating heating element 34. Rigid attachment could be accomplished by welding, soldering, fastening, riveting, gluing, fusing, epoxy, or similar.

The distal end of second floating conductor rod 32 is rigidly attached to the second end 38 of floating heating element 34. Rigid attachment is end-to-end such that the longitudinal axis of second floating conductor rod 32 is coincident with the longitudinal axis of second end 38 of floating heating element 34. Rigid attachment is such that there is electrical conductivity and continuity between second floating conductor rod 32 and second end 38 of floating heating element 34. Rigid attachment could be accomplished by welding, soldering, fastening, riveting, gluing, fusing, epoxy, or similar.

The above described slideable attachment of floating heating element 34 and slideable attachment of first and second floating conductor rods 30,32 can be called a "floating attachment", hence the characterization of "floating" heating element 34 and first and second "floating" conductor rods 30,32. The above described slideable attachment of floating heating element 34 and slideable attachment of first and second floating conductor rods 30,32 each function to prevent mechanical stress build-up on floating heating element 34 and its connections to the electrical power source resulting from thermal expansion and contraction and thermal stress. As the vaporizer 5 is turned on, heated and up, and used, the floating heating element 34 can expand by as much as an inch or more in overall length as a result of thermal expansion from raising the temperature of the heating element from room temperature to more than 500 degrees Fahrenheit. The heating element must be maintained at a hotter temperature than the sublime temperature of oxalic acid at 370-400 degrees Fahrenheit for proper operation of vaporizer 5. The longitudinal windings of the floating heating element 34 cause the thermal expansion to occur more longitudinally. The slideable attachment of first and second floating conductor rods 30,32 then in turn allows the longitudinal expansion of the floating heating element 34 to shift first and second floating conductor rods 30,32 upwards and into the proximal direction to further protrude or penetrate into electrical box 20 when heated up. This further protrusion or penetration of first and second floating conductor rods 30,32 is then taken up by the slack in internal electrical wiring 25, without loss of electrical connections and without causing any new stresses on the electrical connections. First and second floating conductor rods 30,32 slide back and forth within first and second floating conductor rod electrical shields 26,27 which remain motionless because of their rigid connection to integral body tube 10 through floating heating element electrical shield 28 and electrical box 20. The above described design greatly extends the lifetime of the vaporizer and is a far superior design to previous vaporizers that do not include: first and second floating conductor rods 30,32; first and second floating conductor rod electrical shields 26,27; and at least four floating conductor rod slide bushings 33.

Oxalic acid vaporizer with integral body tube, detachable proximal end air nozzle, and floating heating element 5 further comprises a detachable pneumatic box assembly 41. Detachable pneumatic box assembly 41 comprises: a detachable pneumatic box 40, a pneumatic box clamp 42, an air hose connector 44, a pneumatic valve 46, and a nozzle tube fitting 48. Detachable pneumatic box 40 is a rigid hollow enclosure that functions to house and protect pneumatic valve 46 and nozzle tube fitting 48. Detachable pneumatic box 40 could be any type of protective enclosure. Detachable pneumatic box 40 has and interior and an exterior. There is an access hole or gap on detachable pneumatic box 40 to provide access to the second end of nozzle tube fitting 48. Detachable pneumatic box 40 has an upper surface located on its exterior proximal end and a lower surface located on its exterior distal end. Detachable pneumatic box 40 is reversibly attached to the exterior surface of integral body tube 10 with its lower surface adjacent to the upper surface of electrical box 20. Detachable pneumatic box 40 is reversibly attached to the exterior surface of integral body tube 10 by pneumatic box clamp 42. Pneumatic box clamp 42 is a clamp that is reversibly attachable to the exterior surface of integral body tube 10. Pneumatic box clamp 42 is a typical clamp and can be any known type of clamp or clamping means. Pneumatic box clamp 42 has a tension position and a release position. In the tension position, pneumatic box clamp 42 applies inward radial pressure on the exterior surface of integral body tube 10, which functions to form a rigid connection onto the exterior surface of integral body tube 10. In the release position, the inward radial pressure on the exterior surface of integral body tube 10 is released to yield zero pressure on the exterior surface of integral body tube 10. In the release position, there is clearance between clamp and the exterior surface of integral body tube 10. Typically, a clamp handle or fastener 43 is used to switch back and forth between the clamp position and the release position. Air hose connector 44 is a typical connector or fitting used to connect to an air compressor line or pressurized air line. Air hose connector 44 has a first end and a second end. The first end of air hose connector 44 is reversibly attachable to a typical air compressor line or pressurized air line. Connection to an air compressor line or pressurized air line is required for the operation of oxalic acid vaporizer with integral body tube, detachable proximal end air nozzle, and floating heating element 5. Pneumatic valve 46 is a pneumatic valve that is engineered to adjust the flow of gas or air there though. Pneumatic valve 46 has a first end and a second end. The first end of pneumatic valve 46 is plumbed to the second end of air hose connector 44. The term plumbed is used to describe the sealing together of a pipe, tube, or fitting with another pipe, tube, or fitting to yield an airtight connection there between that may be accomplished by any known means such as welding, soldering, threading, compression press fit, gluing, epoxying, or other. Pneumatic valve 46 must have a fine adjustment to allow for fine adjustments of the quantity of air flowing there through. Pneumatic valve 46 can be any known type of air valve or pneumatic valve with a relatively fine adjustment. Pneumatic valve 46 may be a ball valve, gate valve, needle valve, or any other known type of valve. Pneumatic valve 46 includes a valve handle 47 that extends through detachable pneumatic box 40 and is located on the exterior of detachable pneumatic box 40. Valve handle 47 is used to adjust the flow rate of air through pneumatic valve 46. Nozzle tube fitting 48 is a pneumatic fitting that is reversibly attachable to nozzle tube 52. Nozzle tube fitting 48 can be any known type of air line fitting or pneumatic fitting. Nozzle tube fitting 48 has a first end and a second end. The first end of nozzle tube fitting 48 is plumbed to the second end of pneumatic valve 46. The second end of nozzle tube fitting 48 is reversibly attachable to the distal end 54 of nozzle tube 52. Nozzle tube fitting 48 can be any known type of air line fitting or pneumatic fitting that can be reversibly attached to nozzle tube 52.

Oxalic acid vaporizer with integral body tube, detachable proximal end air nozzle, and floating heating element 5 further comprises: a detachable proximal end air nozzle assembly 50. Detachable proximal end air nozzle assembly 50 comprises: a nozzle tube 52, a locating collar 56, and a nozzle tube shield 58. Nozzle tube 52 is a rigid hollow tube with an interior and an exterior. Nozzle tube 52 has a proximal end 53 and a distal end 54. Nozzle tube 52 is capable of retaining pressurized gas or air within its interior without leaking. Nozzle tube 52 may be made from any know material such as metal, glass, plastic, ceramic, carbon fiber, composite, or other material. The proximal end 53 of nozzle tube 52 has a 180-degree bend or U-shape as depicted. This 180-degree bend or U-shape is used to redirect and aim the flow of pressurized gas longitudinally back down the integral body tube 10. When detachable proximal end air nozzle assembly 50 is properly attached and located onto integral body tube 10, the proximal end 53 of nozzle tube 52 penetrates the proximal end of integral body tube 10 and is in the interior of integral body tube 10. The distal end 54 of nozzle tube 52 has a 90-degree bend or elbow that mates with or reversibly attaches to the second end of nozzle tube fitting 48. The 90-degree bend or elbow allows the distal end 54 of nozzle tube 52 to be directed into nozzle tube fitting 48. Reversible attachment may be accomplished by any known means. In best mode, reversible attachment is accomplished by a compression fitting. Locating collar 56 is a rigid hollow cylindrical member with an interior, and exterior, an inner diameter, an outer diameter, and open ends. The inner diameter of locating collar 56 is sized to make a slip fit over the outer diameter integral body tube 10. Nozzle tube shield 58 is a shield member with an inner side and an outer side. Nozzle tube shield 58 functions to protect the nozzle tube 52 from exterior damage. Nozzle tube shield 58 also helps locate and attach nozzle tube 52 to the proximal end of integral body tube 10. Nozzle tube 52 is rigidly attached to the inner side of nozzle tube shield 58. The inner side of nozzle tube shield 58 is rigidly attached to the exterior of locating collar 56. Nozzle tube 52, locating collar 56, and nozzle tube shield 58 are sized, aligned, and attached together so that the distal end 54 of nozzle tube 52 aims directly down the center of integral body tube 10 when locating collar 56 is slid over the proximal end of integral body tube 10 as depicted.

In order to use oxalic acid vaporizer with integral body tube, detachable proximal end air nozzle, and floating heating element 5, the detachable pneumatic box 40 and the detachable proximal end air nozzle assembly 50 must be attached onto integral body tube 10 as depicted in FIG. 1. In order to clean oxalic acid vaporizer with integral body tube, detachable proximal end air nozzle, and floating heating element 5, the detachable pneumatic box 40 and the detachable proximal end air nozzle assembly 50 are detached from integral body tube 10 as depicted in FIG. 2. Importantly, the detachable proximal end air nozzle assembly 50 allows for separate cleaning of the nozzle tube 52 in a sink or washtub with water and harsh solvents or detergents without getting the water and harsh solvents or detergents on floating heating element 34, internal electrical wiring 25, or integral body tube 10. Also importantly, the detachable pneumatic box 40 and the detachable proximal end air nozzle assembly 50 remain separately detachable from each other so that nozzle tube 52 and the rest detachable proximal end air nozzle assembly 50 may be washed separately in a sink or washtub with water and harsh solvents or detergents without getting the water and harsh solvents or detergents on pneumatic valve 46, air hose connector 44 or any other components in detachable pneumatic box 40. The above-described design greatly extends the lifetime of the vaporizer and is a far superior design to previous vaporizers that do not include a detachable pneumatic box assembly 41 or a detachable proximal end air nozzle assembly 50.

What is claimed is:

1. An oxalic acid vaporizer comprising: an integral body tube; an internal powder baffle; an electrical box; and a detachable proximal end air nozzle assembly, wherein,
    said integral body tube is a rigid hollow cylindrical member with an interior surface defining an interior of said body tube, an exterior surface, a proximal end, a distal end, and a longitudinal axis running along a length of said rigid hollow cylindrical member,
    said exterior surface of said integral body tube is without any holes, perforations, punctures, gaps, vents, or discontinuities,
    said interior surface of said integral body tube is without any holes, perforations, punctures, gaps, vents, or discontinuities,
    said internal powder baffle is a rigid oblong planar member with a left side, a right side, a lower end, an upper end, and a longitudinal axis running through said lower and upper ends,
    said internal powder baffle is positioned and located within said interior of said body tube,
    said internal powder baffle is positioned and located so that said longitudinal axis of said internal powder baffle is askew from said longitudinal axis of said body tube,
    said left side, said right side, and said lower end of said internal powder baffle are each rigidly attached or connected to said interior surface of said body tube,
    said upper end of said internal powder baffle is not attached or connected to said interior surface of said body tube,
    said electrical box is a rigid hollow enclosure with electrical wiring therein,
    said electrical box is rigidly attached to said exterior surface of said body tube,
    said detachable proximal end air nozzle assembly is attachable to the proximal end of said body tube and comprises a nozzle tube that is a rigid hollow tube with an interior, an exterior, a proximal end, and a distal end,
    said proximal end of said nozzle tube has a 180-degree bend or U-shape, and
    said distal end of said nozzle tube has a 90-degree bend or elbow.

2. An oxalic acid vaporizer as recited in claim 1 further comprising a detachable pneumatic box assembly that comprises: a pneumatic box clamp, an air hose connector, a pneumatic valve, and a nozzle tube fitting, wherein,
    said pneumatic box clamp is reversibly attachable to said exterior surface of said integral body tube, said air hose connector is a connector used to reversibly attach to an air compressor line or a pressurized air line, said pneumatic valve is a valve that is engineered to adjust a flow of gas or air there though, and
    said nozzle tube fitting is reversibly attachable to the distal end of said nozzle tube.

3. An oxalic acid vaporizer comprising: a body tube; an internal powder baffle; an electrical box; at least two floating heating element saddles; and a floating heating element, wherein,
    said body tube is a rigid hollow cylindrical member with an interior surface defining an interior of said body tube, an exterior surface, a proximal end, a distal end, and a longitudinal axis running along a length of said rigid hollow cylindrical member,
    said internal powder baffle is a rigid oblong planar member with a left side, a right side, a lower end, an upper end, and a longitudinal axis running through said lower and upper ends, said internal powder baffle is positioned and located within said interior of said body tube,
    said internal powder baffle is positioned and located so that said longitudinal axis of said internal powder baffle is askew from said longitudinal axis of said body tube,
    said left side, said right side, and said lower end of said internal powder baffle are each rigidly attached or connected to said interior surface of said body tube,
    said upper end of said internal powder baffle is not attached or connected to said interior surface of said body tube,
    said electrical box is a rigid hollow enclosure with electrical wiring therein, said electrical wiring is connected to said floating heating element,
    said electrical box is rigidly attached to said exterior surface of said body tube,
    each of said at least two floating heating element saddles is a rigid arch-shaped, bow-shaped, or U-shaped member with a concave side and a convex side,
    each of said at least two floating heating element saddles is rigidly attached to said exterior surface of said body tube and oriented so that said concave side is aligned with said longitudinal axis of said body tube and faces said proximal end of said body tube and said convex side is aligned with said longitudinal axis of said body tube and faces said distal end of said body tube,
    said floating heating element is a heating element with longitudinal windings that run longitudinally along the length of said rigid hollow cylindrical member, and
    said floating heating element is slideably attached to said exterior surface of said body tube adjacent to and contiguous with each of said at least two floating heating element saddles.

4. An oxalic acid vaporizer comprising: a body tube; an internal powder baffle; an electrical box; a first floating conductor rod; a second floating conductor rod; a first floating conductor rod electrical shield; a second floating conductor rod electrical shield; and at least four floating conductor rod slide bushings, wherein,
    said body tube is a first rigid hollow cylindrical member with an interior surface defining an interior of said body tube, an exterior surface, a proximal end, a distal end, and a longitudinal axis running along a length of said first rigid hollow cylindrical member, said internal powder baffle is a rigid oblong planar member with a left side, a right side, a lower end, an upper end, and a longitudinal axis running through said lower and upper ends, said internal powder baffle is positioned and located within said interior of said body tube, said internal powder baffle is positioned and located so that said longitudinal axis of said internal powder baffle is askew from said longitudinal axis of said body tube, said left side, said right side, and said lower end of said internal powder baffle are each rigidly attached or connected to said interior surface of said body tube, said upper end of said internal powder baffle is not attached or connected to said interior surface of said body tube, said electrical box is a rigid hollow enclosure with electrical wiring therein, said electrical wiring is connected to said first and second floating conductor rods, said electrical box is rigidly attached to said exterior surface of said body tube, said first and second floating conductor rod electrical shields are each a second rigid hollow cylindrical member with open ends, said first and second floating conductor rod electrical shields each have an inner diameter, an outer diameter, an interior surface defining an interior of each of said first and second floating conductor rod electrical shields, an exterior surface, and a longitudinal axis running along a length of said second rigid hollow cylindrical member, said first and second floating conductor rod electrical shields are positioned and located with each of their said longitudinal axes parallel with each other and with said longitudinal axis of said body tube, said first and second floating conductor rod electrical shields are positioned and located on said exterior of said body tube with a clearance space between said exterior surfaces of said first and second floating conductor rod electrical shields and said exterior surface of said body tube, said first and second floating conductor rods are each a rigid solid cylindrical member with a diameter, a proximal end, a distal end, and a longitudinal axis running along a length of said rigid solid cylindrical member, each of said at least four floating conductor rod slide bushings is an annular shaped member or ring shaped member with an outside diameter, an inside diameter, and a thickness, said inside diameter of each of said at least four floating conductor rod slide bushings is sized to make a slip-fit with said outside diameter of said first and second floating conductor rods, a first pair of said at least four floating conductor rod slide bushings are located and positioned within said interior of said first floating conductor rod electrical shield with said first floating conductor rod located and positioned within said inside diameters of said first pair of said at least four floating conductor rod slide bushings, and a second pair of said at least four floating conductor rod slide bushings are located and positioned within said interior of said second floating conductor rod electrical shield with said second floating conductor rod located and positioned within said inside diameters of said second pair of said at least four floating conductor rod slide bushings.

* * * * *